(12) United States Patent
Lin et al.

(10) Patent No.: US 7,638,332 B2
(45) Date of Patent: Dec. 29, 2009

(54) LOW PRESSURE GAS ACCELERATED GENE GUN

(75) Inventors: Hao-Jan Lin, Taipei (TW); Ying-Chang Wang, Changhua (TW); Cheng-Hsien Chen, Taipei (TW)

(73) Assignee: BioWare Technology Co., Ltd., Taipei Hsien (TW)

( * ) Notice: Subject to any disclaimer, the term of this patent is extended or adjusted under 35 U.S.C. 154(b) by 275 days.

(21) Appl. No.: 10/735,602

(22) Filed: Dec. 12, 2003
(Under 37 CFR 1.47)

(65) Prior Publication Data

US 2004/0180442 A1 Sep. 16, 2004

Related U.S. Application Data

(60) Provisional application No. 60/444,775, filed on Feb. 3, 2003.

(51) Int. Cl.
| | |
|---|---|
| *C12N 15/63* | (2006.01) |
| *C12N 15/82* | (2006.01) |
| *C12M 1/00* | (2006.01) |
| *C12N 15/87* | (2006.01) |

(52) U.S. Cl. .................... 435/455; 435/470; 435/285.3
(58) Field of Classification Search .................... None
See application file for complete search history.

(56) References Cited

U.S. PATENT DOCUMENTS

| | | | | |
|---|---|---|---|---|
| 3,914,573 | A * | 10/1975 | Muehlberger | 219/76.16 |
| 4,945,050 | A | 7/1990 | Sanford et al. | 45/172.1 |
| 6,004,287 | A * | 12/1999 | Loomis et al. | 604/68 |
| 6,273,789 | B1 * | 8/2001 | LaSalle et al. | 451/38 |
| 6,436,709 | B1 * | 8/2002 | Lin et al. | 435/459 |
| 2002/0013283 | A1 * | 1/2002 | Tomalia et al. | 514/44 |
| 2004/0033589 | A1 * | 2/2004 | O'Brien | 435/285.3 |

FOREIGN PATENT DOCUMENTS

| | | |
|---|---|---|
| WO | WO 9100915 | 1/1991 |
| WO | WO 94/24263 * | 10/1994 |
| WO | WO 01/29233 A2 * | 4/2001 |
| WO | WO 0244391 | 6/2002 |
| WO | WO 03/086510 | 10/2003 |

OTHER PUBLICATIONS

Bhat et al. (J. Appl. Genet. 2001, 42(4): 405-412).*
The American Heritage® Dictionary of the English Language: Fourth Edition. 2000, http://www.bartleby.com/61/33/S0553300.html.*
Bodey et al. (2000) Anticancer Res. 20:2665-2676.*
Hersey et al. (1999) Pharmacol. Ther. 81:111-119.*
Platsoucas et al. (2003) Anticancer Res. 23:1969-1996.*
Nawroki et al. (2001) Expert Opin. Biol. Ther. 1:193-204.*
Verma et al. (1997) Nature 389:239-242.*
Marshall (1995) Science 269:1050-1055.*
Eck et al. (1996) Goodman & Gilman's The Pharmacological Basis of Therapeutics, 9th Edition, Chapter 5, McGraw-Hill, NY.*
Ross et al. Human gene Therapy 7:1781-1790.*
Lavigne (2006) Expert Opin. Emerging Drugs (2006) 11:541-557.*
Lin et al. (2000) Int. J. Dermatol. (2000) 39:161-170.*

* cited by examiner

*Primary Examiner*—Quang Nguyen
(74) *Attorney, Agent, or Firm*—J.C. Patents

(57) ABSTRACT

The present invention relates to a gene gun and the application of the gene gun for gene transformation. A low pressure gas is used in the gene gun to directly accelerate the biological material containing solution, so that the biological materials penetrate through the cell membrane/wall or the skin of an animal, without using metal particle carriers, for gene transformation.

14 Claims, 5 Drawing Sheets
(3 of 5 Drawing Sheet(s) Filed in Color)

LOW PRESSURE GAS ACCELERATED GENE GUN

CROSS-REFERENCE TO RELATED APPLICATION

This application claims the priority benefits of U.S. provisional application titled" "GOLD PARTICLE-FREE GENE GUN BY FLUID FLOW-BOMBARDMENT" filed on Feb. 3, 2003, Ser. No. 60/444,775. All disclosure of this application is incorporated herein by reference.

BACKGROUNDING OF THE INVENTION

1. Field of Invention

The present invention relates to a gene gun system. More particularly, the present invention relates to a gene gun system and the application of the gene gun system for gene transformation, wherein under a low pressure, the gene gun system using a gas is able to accelerate the biological material containing solution to a high speed, so that the biological materials penetrate through the cell membrane/wall or skin of a animal, without using metal particle carriers and gene transformation is accomplished with only low pressure.

2. Description of Related Art

Following the discovery of the genetic materials and rapid developments in genetics, scientists now can skillfully practice genetic engineering technology, for example, introducing foreign genes to control the natures of a cell or even an organism. It has been widely applied in basic scientific studies and in improvements of agricultural products that heterologous genetic materials, such as DNAs, are transferred to the host cells in order to change the biological characteristics and morphology. For instance, genetic engineering helps to improve the insect resistance, the frost resistance or the nutrient compositions in agricultural products. In recent years, the gene transformation technology, in the forms of gene therapy or gene vaccines, has been applied in treating human diseases. Due to the successful application of the gene transformation technology in the medical field, clinical treatments of quite a few genetic diseases including cancers have significant breakthroughs.

Gene transformation can be conducted in several different approaches and the earliest approach is to use bacterial plasmids or viral vectors as medium carriers for delivering genes into the cytoplasma of the animal or plant cells. Though constantly developed and improved, it is difficult to overlook the side effects, including non-specific immune responses and genetic recombination, of the bacterial plasmids or viral vectors and the resultant risks when applied in medical treatments. On the other hand, free of using bacterial or viral carriers, other physical or mechanical approaches of gene transformation, such as, electro-perforation and micro-injection, can avoid the side effects of these carriers and be applied for therapeutic purposes. However, the stability and success rate are low and the operation is laborious.

In recent years, gene transformation using a physical approach has been applied in empirical practices. The physical approach, particle gun, is to accelerate gold particles carrying the biological materials (e.g. DNAs) into the cells for gene transformation or gene transfer. Particle gun is also applicable to the research and development of other fields, for example, plants, mammalian somatic cells, gene therapy, and the recently developed DNA vaccination.

The particle gun system uses DNA-coated gold particles within a sample cartridge and a gas to accelerate the tube based on the high pressure shock wave principle. When a preset high pressure is reached in the pressurized chamber, the sample cartridge having DNA-coated particles is accelerated by a resulting shock wave into a stopping screen. The DNA-coated particles continue to accelerate to enter the target tissue due to the inertia effect. A major disadvantage of the aforementioned methods is the loud noise resulting from the shock wave. The high speed and high pressure gas that is generated by the shock wave also causes cell deaths. Moreover, the gas used in the conventional particle gun technique employs the expensive helium gas and costly gold particles are required as carriers.

Although it is feasible to use particle gun using the gene carrying gold particles, the gold particles regularly cause damages to the cells or the interactions between the metal particles and the carried biological materials induce structural changes of the biological materials, thus hampering the clinical effects. Moreover, the operation of the particle gun is inconvenient to the user, because the preparation of the DNA-coated gold particles is complicated and troublesome. For therapeutic purposes, an effective and convenient gene delivery tool is needed for specific attenuated vaccines expressed through the epidermal tissues, virions for gene therapy or reagents for clinical tests. Especially, this gene delivery tool can dependably deliver the genetic or biological materials without causing significant variations.

SUMMARY OF THE INVENTION

Based on the theory of aerodynamic and the bi-phase flow theory, the present invention provides a low-pressure gas accelerated gene gun, wherein the problems of low noise, cell death induced by shock wave and the application of the expensive helium gas or gold particles are prevented. The gene gun of this invention can be applied to deliver various kinds of biological or genetic materials into the cell.

To resolve the aforementioned problems, the present invention provides a gene gun, which is operable under a low pressure, using a gas (a nitrogen gas, a helium gas or even air) to directly accelerate biological material containing solution to an extreme high speed, for example, greater than 200 m/sec, free of using the micro-carriers (gold particles or tungsten particles). The biological materials can penetrate through the epidermal tissues of animal or the cell membrane/wall and enter into cytoplasma or the cell nucleus to express the special protein and to generate the new biological function.

The present invention provides a gene gun, wherein the gene gun is applicable in gene transformation. According to a preferred embodiment of the present invention, the contour design of the spray nozzle of the gene gun and modification of the gene gun operation allows the gene gun to operate at a pressure lower than 4 atm. and accelerate the sample solution to an extreme high speed. Without being carried by the metal particles, the biological materials can penetrate the epidermis or the cell/membrane/wall and enter into the cell or the organism.

Since a low pressure is used, the biological materials are driven into the cell without using metal particles, to achieve gene transformation with minimal noise and damages to the cells. Moreover, due to the lower pressure for the gene gun operation, the consumption of the gas and the operation cost is reduced along with decreased noise, in the present invention.

Since the sample of this invention is prepared in the solution form without using metal particles, the operation of the gene gun is easy and straightforward, disregarding the difficulties conventionally encountered in the preparation of the gold particles. In the present invention, the biological material, for example, DNAs, RNAs, proteins, virions or drugs, is prepared in the solution form and accelerated to enter into the cell for delivery or gene transformation. Since the operation of the gene gun free of metal particles for carrying the biological materials, risks of altering the biological material are lowered and damages to the target cells are lessened. The gene gun of this invention can deliver the biological material into the cell or the organism, and can be applied in the fields of immuno-vaccines, immuno-therapy, cancer treatments or gene therapy.

It is to be understood that both the foregoing general description and the following detailed description are exemplary, and are intended to provide further explanation of the invention as claimed.

BRIEF DESCRIPTION OF THE DRAWINGS

The file of this patent or application contains at least one drawing executed in color. Copies of this patent or patent application publication with color drawing(s) will be provided by the patent and Trademark Office upon request and payment of the necessary fee. The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE PREFERRED EMBODIMENTS

Figure 1:
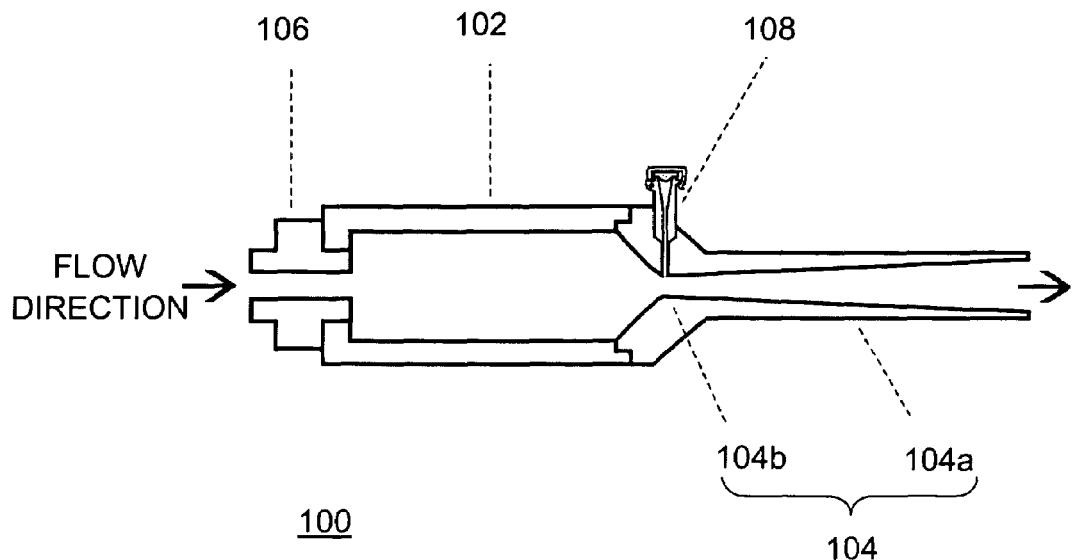
FIG. 1 is a cross-sectional view of a gene gun according to a preferred embodiment of the present invention.

Referring to FIG. 1, FIG. 1 is a cross-sectional view of a gene gun 100 according to a preferred embodiment of the present invention. The gene gun 100 of the present invention is divided into four parts, comprising at least a pressurized chamber 102, a sprayer 104, a backside connector 106 and a material delivery system 108. The backside connector 106 is connected to the high pressure gas source (FIG. 2) via valves. A gas (flow direction shown as arrow) is delivered from the backside connector 106 to the pressurized chamber 102. As the gas in the pressurized chamber 102 is built up to a preset pressure, the high-pressure gas and the sample solution carried by the high-pressure gas are sprayed out through the sprayer 104. The material of the pressurized chamber is a light metal, for example, aluminum alloy. The material of the sprayer 104 is a biocompatible metal, for example, stainless steel or its alloys.

In general, the sample solution (i.e. biological material containing solution) is accelerated by a gas to a velocity of about 200 to 300 meter/sec, and this speed does not exceed the speed of sound. The sprayer 104, as shown in FIG. 1, includes at least a terminal spray tube 104*a* and a nozzle 104*b*. According to the theory of aerodynamics, as the pressure difference between the internal and the external of the spray nozzle is greater than 1.8 atm, a supersonic flow is generated. If the cross-sectional diameter of the nozzle converges initially and then diverges to a small degree, a supersonic flow is generated in the nozzle 104*b*. The gas velocity gradually decreases as the gas enters the spray tube 104*a*. Increasing the length of the spray tube 104*a*, the gas velocity decreases. The gas velocity can thereby be controlled within a certain limits according to the length of the spray tube 104*a*.

According to a preferred embodiment of the present invention, an appropriate design includes an application of sample solution without micro-carriers and a material delivery system as disclosed in the present invention. The sample solution can uniformly be accelerated to a required velocity without the application of high pressure, thus mitigating the damage to the target cells. Moreover, the contour design of the spray nozzle 104*b* and the spray tube 104*a* allows the pressure at the exit of the spray nozzle to approach the atmospheric pressure. Damages to the target cells are thereby reduced. According to one preferred embodiment of the present invention, the gene gun operation uses the sample solution without containing particle carriers in the solution, in combination of a special spray nozzle of the gene gun. In accordance of this special spray nozzle, the sample solution can be accelerated to different speeds by varying the length of the terminal spray tube and the type of gas source.

The design of the material delivery system 108 can be adjusted according to the operation requirements. As exemplified, a gravity dispensing mechanism is employed to release droplets of the sample solution from the material delivery system. The sample solution droplets are then carried away by the high velocity gas flow and are discharged at a high speed into the target tissue. The sample solution can be injected into an inner cavity of the material delivery system 108 through an inlet, while the inner cavity is big enough to hold the sample solution. The sample solution flows through the channel that is connected to the inner cavity to the outlet and is steadily released as droplets around the spray neck. Alternatively, the material delivery system can further includes a delayed release loading station, so that the sample solution droplets are placed on the loading station, waiting to be carried away by the gas flow. Other mechanisms, such as viscosity control, can be used to achieve the delayed release function. In addition, a control valve can be incorporated into the material delivery system to control the release of the sample solution, or the release amount, depending on whether the gene gun discharges one single shot or multiple shots.

Alternatively, the material delivery system 108 can be designed to facilitate the operation in single shot. Before shooting, the spray neck can be separated from the pressurized chamber and the sample solution is loaded on the spray neck. Once the spray neck is connected with the pressurized chamber, the sample solution is ready to be discharged. During operation, the sample solution is exposed to the high-velocity gas flow. The high-velocity gas flow would carry the sample solution out of the spray neck and the sample solution is further accelerated to the required velocity by the sprayer 104.

Figure 2:
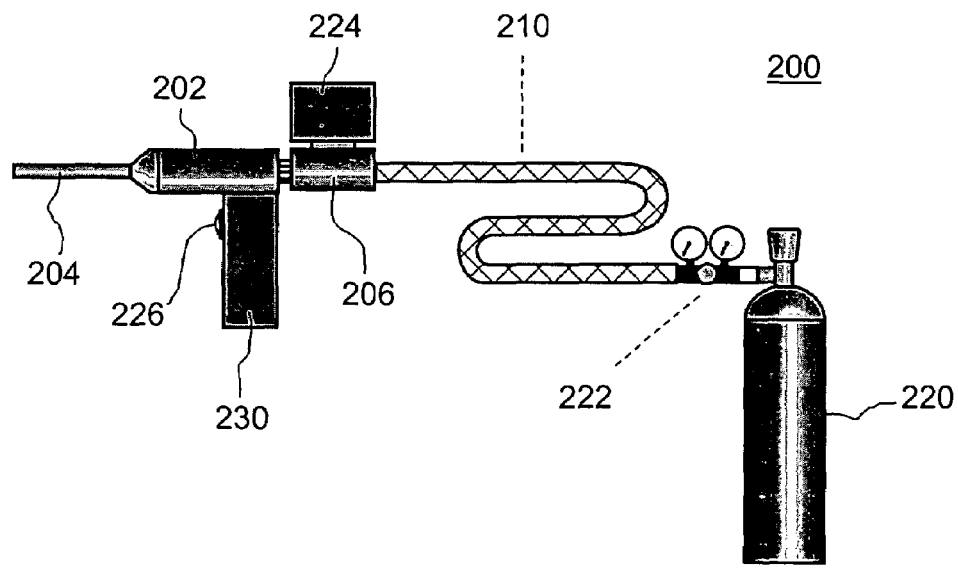
FIG. 2 illustrates the connection between the gene gun and tube assembly.

FIG. 2 illustrates the entire gene gun system. The gas source for the gene gun system 200 is provided from a gas tank 220. The gas source from the gas tank 220 includes a helium gas, a nitrogen gas or other type of gas or air. The helium gas can travel at velocity greater than 1000 m/s. Moreover, less damage is inflicted upon the target cell because the mass of helium is lower. Helium is thus an ideal gas, except for being too expensive. Using helium gas is essential on animal or plant cells with a thicker keratin or wax layer. However, using a nitrogen gas for the gene gun is sufficient for the easily penetrated biological system. The gas in the gas tank 220 is set at a certain pressure by a pressure regulator 222. The pressure in the pressurized tank of the gene gun has to be greater than 1.8 atm. Due to the drop of the gas pressure in the tubing, the pressure regulator 222 has to set at a higher pressure.

As shown in FIG. 2, the gas is passed from the gas tank 220 through the pressure regulator 222 and the tubing 210. A control valve 224 is further used to determine whether the gas would enter the pressurized chamber 202 through the backside connector 206. The control valve 224 is controlled by a controller (not shown). When the gene gun system 200 is operating, the pressure regulator 222 is set at an appropriate pressure. The biological material containing solution (sample solution) is placed in the gene gun. The biological material can be RNAs, DNAs, proteins, peptides, saccharides, virions, or drugs, for example. The trigger device 226 that is connected to the handle structure 230 of the gene gun system is initiated, the controller is set off, sending a signal to open the control valve 224. The gas flows into the pressurized chamber 202, and after the establishment of the fluid flow field, the sample solution is then carried out by the high-velocity gas flow and is discharged into the target tissue through the sprayer 204.

Though the structure of the gene gun of the present invention includes a handle structure and a triggering device, the handle structure and the triggering device are not limited to any single type of technology or assembly. Any existing assembly or technology for the handle structure or the triggering device can be used. Since the handle structure and the triggering device are not the essential features of the present invention, details for the handle structure and the triggering device will not be reiterated. It is intended that the specification and examples to be considered as exemplary only. Additional advantages and modifications are readily occurred to those skilled in the art from the consideration of the specification and the practice of the invention disclosed herein.

Figure 3:
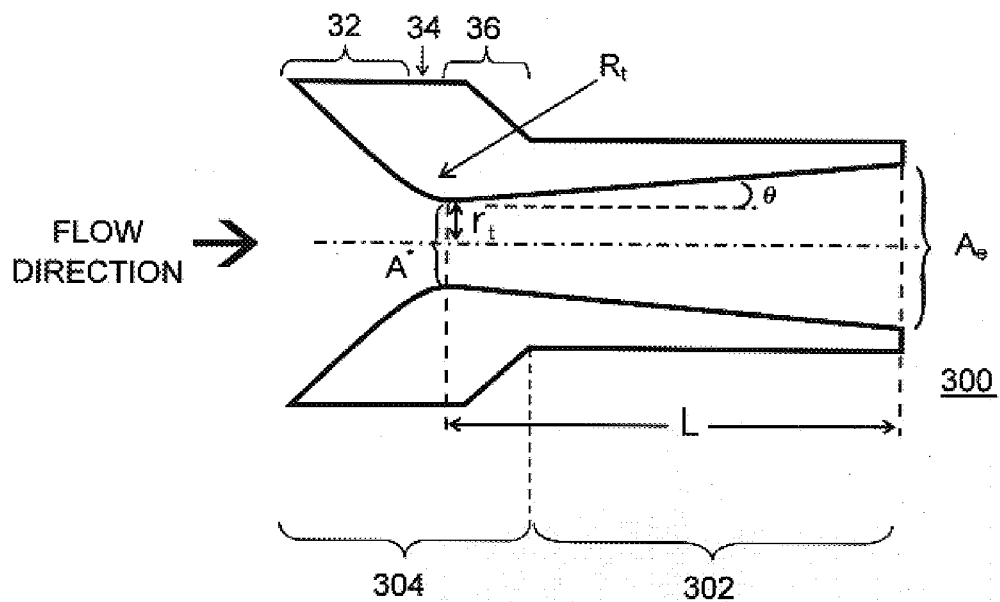
FIG. 3 is a cross-section view of a sprayer and a spray nozzle according to a preferred embodiment of the present invention.

In order for the sample solution droplets to travel at a high speed, the present invention provides a high-speed sprayer 300, as shown in FIG. 3. Unlike the conventional straight spray tube, the spray tube 302 of the present invention is conical shape, allowing the speed of the gas flow to achieve the supersonic flow rate and the speed of the sample solution to approach the speed of sound. The spray nozzle 304 comprises a contour entrance, allowing the discharged sample solution to be more evenly distributed and are not localized at the exit, which causes cell death. Moreover, the gas pressure at the exit of the spray nozzle approaches atmospheric pressure to mitigate damages to the cell.

The spray tube and the spray nozzle of the present invention are designed according to the following theory:

Assuming the flow field is an isentropic flow, the ratio of the area of the spray nozzle (Ae) and the area of the spray neck A* is $$\frac{Ae}{A^*} = \frac{1}{Me}\left[\frac{2}{\gamma+1}\left(1+\frac{\gamma-1}{2}Me^2\right)\right]^{\frac{\gamma+1}{2(\gamma-1)}}$$

wherein, Me is the Mach number, which is a ratio of the gas flow rate over the speed of sound and γ is the specific heat ratio. If Me, Ae and γ are defined, A* is determined.

Similarly, if the pressure at the exit of the spray nozzle, the pressure in the pressurized chamber Po can also be determined according to the following equation $$Po = P\left(1+\frac{\gamma-1}{2}Me^2\right)^{\frac{\gamma}{\gamma-1}}.$$

If the pressure in the pressurized chamber is the gas tank pressure, the required pressure in the gas tank Pc is determined according to the following equation $$Pc = P\left(1+\frac{\gamma-1}{2}M_{in}^2\right)^{\frac{\gamma}{\gamma-1}}\frac{1}{Ld}$$

wherein Ld is dump loss.

Since a certain gas flow rate is needed to carry out the sample solution, the necessary gas tank pressure is resulted by defining the Mack number at the entrance of the pressurized chamber ($M_{in}$).

Moreover, under the steady state condition, the mass flow rate in $m_{in}$ is equal to the mass flow rate out $m_{out}$, $$\dot{m}_{in} = (\rho AV)_{in} = (\rho AV)_{out}$$

$$A_{in}\frac{P_c}{\sqrt{T_o}}\sqrt{\frac{\gamma}{R}}\frac{M_{in}}{\left(1+\frac{\gamma-1}{2}M_{in}\right)^{\frac{\gamma+1}{2(\gamma-1)}}} = A^*\frac{P_0}{\sqrt{T_0}}\sqrt{\frac{\gamma}{R}}\sqrt{\left(\frac{2}{\gamma+1}\right)^{\frac{\gamma+1}{\gamma-1}}}$$

wherein ρ is the gas density, $T_0$ is the temperature in the pressurized chamber, $A_{in}$, which is area of the entrance of the pressurized chamber from the gas tank. $A_{in}$ is thereby easily determined.

FIG. 3 illustrates the contour design of the spray nozzle 304 of the present invention. The spray nozzle 304 is designed to comprise a converging part 32 and a diverging part 36. The transition region between the converging part 32 and the diverging part 36 is the spray neck 34. The contour of the spray nozzle 304 is obviated from any abrupt transition to allow a smooth gas flow. A general rule for designing the spray nozzle 304 of the present invention is as follow:

(1) the simplified design, wherein the gas flow rate exiting the spray nozzle is not uniform.

As shown above, $R_t$ represents the curvature radius of the converging part 32 and $r_t$ is the radius of the spray neck 34, wherein $r_t < R_t < 2r_t$ for the converging part of the simplified design. $\theta$, as shown above, is the angle between the diverging part 36 and center axis of the spray nozzle and the spray tube (broken lines), wherein $\theta$ is less than 15 degrees for the converging part of the simplified design. The contour of the converging part of the spray nozzle, is a diverging straight tube, forming a coned shape structure. The angle $\theta$ between the slanted straight line and the center axis is less than 15 degrees, and is preferably between 10 to 15 degrees.

If the friction loss is ignored and the pressure at the converging part is high enough, the gas flow rate should achieve supersonic in the spray tube. Due to the diverging angle $\theta$ of the spray tube, the slant shock wave caused by the supersonic gas flow can be avoided. In general, of the contour of the spray tube is fixed, the expansion ratio of the gas flow and the Me (Mach number at the outlet) are determined. For the same spray tube, if a different gas is used, a different Mach number or a different pressure (P) at the inlet of the spray tube is obtained. Taking the nitrogen gas as an example, the expansion ratio Ae/At (area of the diverging terminal/area of the neck), the relative diameter ratio De/Dt, the minimum length of the diverging part L (1.2 degree in a corn shape) and the pressure at the inlet of the spray tube are listed in the followings.

(A) if $M_e$=1.2, $D_e$=5 mm
P=2.425 (atm.) $A_e/A_t$=1.034 $D_e/D_t$=1.0151
$D_t$=4.925 mm L=3.57 mm
(B) if $M_e$=1.3, $D_e$=5 mm
P=2.771 (atm.) $A_e/A_t$=1.0663 $D_e/D_t$=1.0326
$D_t$=4.842 mm L=7.58 mm
(C) if $M_e$=1.4, $D_e$=5 mm
P=3.182 (atm.) $A_e/A_t$=1.1115 $D_e/D_t$=1.0543
$D_t$=4.7425 mm L=12.356 mm
(D) if $M_e$=1.5, $D_e$=5 mm
P=3.67 (atm.) $A_e/A_t$=1.1762 $D_e/D_t$=1.0845
$D_t$=4.6104 mm L=18.7 mm
(E) if $M_e$=1.6, $D_e$=5 mm
P=4.25 (atm.) $A_e/A_t$=1.2502 $D_e/D_t$=1.118
$D_t$=4.4723 mm L=25.33 mm
(F) if $M_e$=1.2, $D_e$=4 mm
P=2.425 (atm.) $A_e/A_t$=1.034 $D_e/D_t$=1.0151
$D_t$=3.9405 mm L=2.856 mm
(G) if $M_e$=1.3, $D_e$=4 mm
P=2.771 (atm.) $A_e/A_t$=1.0663 $D_e/D_t$=1.0326
$D_t$=3.8736 mm L=6.06 mm
(H) if $M_e$=1.4, $D_e$=4 mm
P=3.182 (atm.) $A_e/A_t$=1.1115 $D_e/D_t$=1.0543
$D_t$=3.794 mm L=9.8886 mm
(I) if $M_e$=1.5, $D_e$=4 mm
P=3.67 (atm.) $A_e/A_t$=1.1762 $D_e/D_t$=1.0845
$D_t$=3.688 mm L=14.96 mm
(J) if $M_e$=1.6, $D_e$=4 mm
P=4.25 (atm.) $A_e/A_t$=1.2502 $D_e/D_t$=1.118
$D_t$=3.5778 mm L=20.26 mm
(K) if $M_e$=1.2, $D_e$=3 mm
P=2.425 (atm.) $A_e/A_t$=1.034 $D_e/D_t$=1.0151
$D_t$=2.9554 mm L=2.14 mm
(L) if $M_e$=1.3, $D_e$=3 mm
P=2.771 (atm.) $A_e/A_t$=1.0663 $D_e/D_t$=1.0326
$D_t$=2.905 mm L=4.549 mm
(M) if $M_e$=1.4, $D_e$=3 mm
P=3.182 (atm.) $A_e/A_t$=1.1115 $D_e/D_t$=1.0543
$D_t$=2.845 mm L=7.416 mm
(N) if $M_e$=1.5, $D_e$=3 mm
P=3.67 (atm.) $A_e/A_t$=1.1762 $D_e/D_t$=1.0845
$D_t$=2.766 mm L=11.22 mm
(O) if $M_e$=1.6, $D_e$=3 mm
P=4.25 (atm.) $A_e/A_t$=1.2502 $D_e/D_t$=1.118
$D_t$=2.6834 mm L=15.198 mm
(P) if $M_e$=1.2, $D_e$=2.5 mm
P=2.425 (atm.) $A_e/A_t$=1.034 $D_e/D_t$=1.0151
$D_t$=2.463 mm L=1.776 mm
(Q) if $M_e$=1.3, $D_e$=2.5 mm
P=2.771 (atm.) $A_e/A_t$=1.0663 $D_e/D_t$=1.0326
$D_t$=2.426 mm L=3.565 mm
(R) if $M_e$=1.4, $D_e$=2.5 mm
P=3.182 (atm.) $A_e/A_t$=1.1115 $D_e/D_t$=1.0543
$D_t$=2.371 mm L=6.180 mm
(S) if $M_e$=1.5, $D_e$=2.5 mm
P=3.67 (atm.) $A_e/A_t$=1.1762 $D_e/D_t$=1.0845
$D_t$=2.305 mm L=9.350 mm
(T) if $M_e$=1.6, $D_e$=2.5 mm
P=4.25 (atm.) $A_e/A_t$=1.2502 $D_e/D_t$=1.118
$D_t$=2.236 mm L=12.665 mm From the above calculations, the pressure P, the diameter of the spray neck Dt and the minimum length of the diverging part L are obtained when the Mach number at the outlet Me and the diameter of the outlet of the spray tube De are fixed. If Dt is fixed as 4.74 mm, pressure P needs to be 3.18 atm. (about 46.75 psi) to obtain Me=1.4. Considering the pressure loss in the whole system, the pressure of the gas after the control valve should be around 90-100 psi, still under the low pressure range of the gas tank.

(2) the uniform gas flow rate design.

The direction of the gas flow, at the spray nozzle, is not parallel to the center axis. In order to provide a gas flow that parallels to the center axis, the expansion wave generated in the spray neck of the above simple design of the diverging part must be compensated by a special curvature design of the spray nozzle.

Since the gas flow rate achieves supersonic at the exit of the spray nozzle, a coned shape spray tube or a straight spray tube is connected to the spray nozzle to accelerate the sample to high a speed, which is proven to be effective in penetrating into the epidermis cell, through the cell wall and/or the cell membrane.

Sample solution preparation. The preparation of the sample solution can be revised and modified based on the containing biological materials, but not limited to any specific technique or procedure. In general, the biological material can be processed and then dissolved in the suitable solution as the sample solution, without using metal particle carriers.

Preparation of DNA Solution

DNA plasmid constructed with the complete protein expression system is dissolved in the sterile distilled water. The prepared solution can be applied directly for the bombardment of the gene gun.

Preparation of Chitosan Oligomer

Chitosan (Sigma C-3646) is dissolved in 6% acetic acid solution in a concentration of 5 mg/mL, followed by adding 8% $KNO_2$ (w/w of chitosan), and reacted under room temperature for 1 hour. After 1 hour, add 0.1N NaOH in a same volume to terminate the reaction, followed by adding absolute alcohol (solution volume/absolute alcohol volume=1/3), then replaced under 4° C. overnight. The mixture is centrifuged (1500 rpm) under 4° C. to collect the precipitate, and the precipitate is re-dissolved in 0.5% acetic acid solution in a concentration of 2 mg/mL and filtered by a 0.45 μm filter.

Preparation of Chitosan Oligomer-CMC Complex

Chitosan Oligomer is mixed with 2 mg/mL carboxymethylcellulose (CMC) in a 3:1 ratio (in volume), and vortexed to obtain the Chitosan Oligomer-CMC complex.

Preparation of DNA-Chitosan Oligomer-CMC Complex 0.3 μl (concentration 1 μg/μl) pEGFP-N2 vector (Clontech) is added with 4 μl Chitosan Oligomer-CMC complex and the mixture is vortexed until homogenous.

Bombardment of mouse skin with DNA solution. The specimen used for the gene gun experiment is BALB/c mice of about a few weeks old. Hair at the abdomen of the mouse is shaved to expose the skin of the mouse. 3-4 week-old Balb/c mice are selected and shaved to expose the abdominal skin. After filling naked DNA or chitosan-CMC-DNA solution into the gene gun, bombardment is performed to the exposed mice skin. The size of the abdominal skin for each mouse can take average four shots of bombardment, with each shot in a volume of 4.3 μl. After one day, the mice are sacrificed to remove the skin for observation under fluorescent microscopy or under microtomy.

Bombardment of mouse skin with EGFP protein. Similar to the bombardment procedure with DNA solution, mice are shaved to expose the abdominal skin. After filling EGFP protein (4 μg) solution into the gene gun, bombardment is performed to the exposed mice skin. After the bombardment, the skin is washed with cleaning solution to wash off the protein remained outside the skin. Afterwards, the mice are sacrificed to remove the skin for observation under fluorescent microscopy or under microtomy.

Frozen section of mice skin. The mice skin is removed and sectioned into cubes, treated with O.C.T. embedding agent (Tissue-Tek, Sakura Finetechnical Co. Ltd.). The tissue is then sectioned into slices of 10 μm thickness by deep-frozen microtome, observed under fluorescent microscopy.

Genetic immunization of Naked DNA bombardment. 3 week-old Balb/c mice are selected and the abdominal skin of the mice is bombarded by the gene gun with 24 μl DNA solution (containing 1.8 μg naked pEGFP DNA vector) once per week for 4 weeks. The bombardment is performed with a helium pressure of 100 psi. From the 1st to 5th week, blood serum is collected by withdrawing blood from the eye socket once per week. Serum is analyzed by Western Blotting. EGFP protein (0.5 μg) is separated by electrophoresis (SDS-PAGE), transferred to the nitrocellulose paper and diluted 100 times by using the serum obtained from the mice, washed three times with TBS buffer (Tris-base 20 mM, NaCl 150 mM, Tween 20 0.3%, pH 7.2) and then treated with anti-mouse IgG conjugated peroxidase (Sigma A-5906). Next, the product is washed four times by TBS buffer and the nitrocellulose paper is developed with LumiGLO™ (KPL 50-60-00 and 50-59-60) for display and recordation.

Results from the Bombardment of the Gene Gun

Bombardment with Naked DNA Solution

Figure 4A:
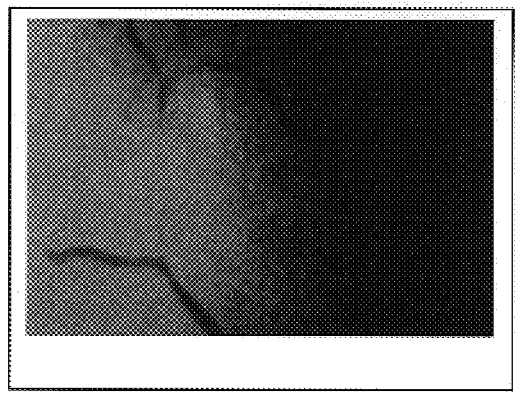
FIG. 4A is a magnified view (40×) of the abdominal epidermis cells of a mouse subsequent to DNA solution bombardment using the gene gun of the present invention.
Figure 4B:
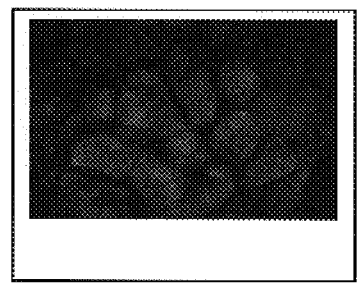
FIG. 4B is a magnified view (400×) of the abdominal epidermis cells of a mouse subsequent to DNA solution bombardment using the gene gun of the present invention.

Shooting (bombardment) is performed with a helium pressure of 60 psi, while each shot includes 0.2 μg DNA. The green fluorescence present on the abdominal epidermis cells of the mice is observed under fluorescence microscopy. As shown in FIG. 4A (40 times magnified, 40×), the left part is the shot region, emitting green fluorescence under the fluorescent microscopy; while the right part is the non-shooting region (not being shot), thus showing no fluorescence. For the shot region of the abdominal region, as shown in FIG. 4B (400×), almost all the epidermis cells show green fluorescence, indicating high efficacy for the bombardment of the gene gun.

Bombardment with Chitosan-DNA Nanoparticles

Figure 5:
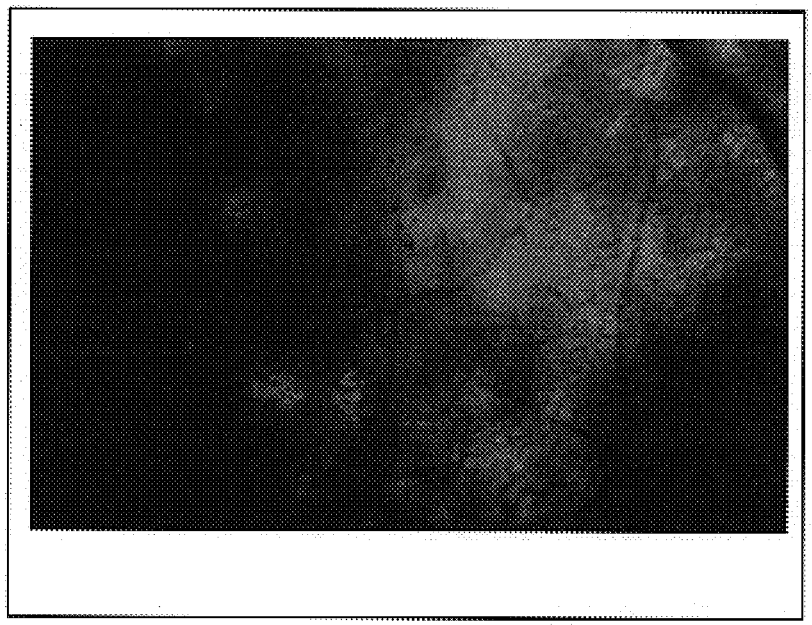
FIG. 5 is a magnified view (40×) of the abdominal epidermis cells of a mouse subsequent to bombardment with chitosan-DNA solution using the gene gun of the present invention.

Shooting is performed with a helium pressure of 50 psi, while each shot includes 0.3 μg DNA (chitosan: CMC=3:1). The green fluorescence present on the abdominal epidermis cells of the mice is observed under fluorescence microscopy. The fluorescent region in FIG. 5 (40×) shows the result of the bombardment with DNA-chitosan nanoparticles. The distribution of green fluorescence is extensive from the bombardment of the gene gun, indicating a desired result of the bombardment.

Bombardment with EGFP Protein

Figure 6:
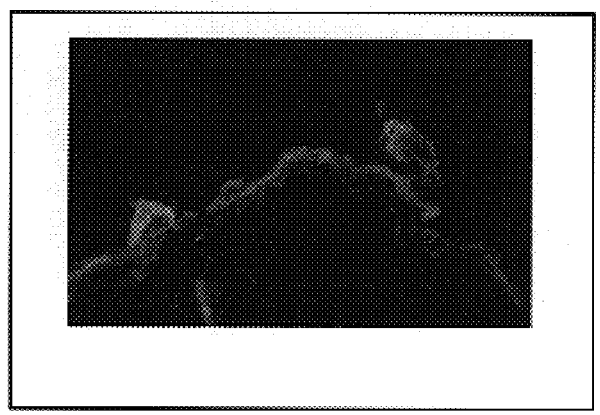
FIG. 6 is a magnified view (400×) of the frozen slice of abdominal epidermis cells of a mouse subsequent to bombardment with EGFP protein solution using the gene gun of the present invention.

Shooting is performed with a helium pressure of 100 psi, while each shot includes 4 μg EGFP protein. The fluorescence present on the abdominal skin of the mice is observed by fluorescent microscopy. From the observed fluorescence result of FIG. 6 (400×) for the frozen section of the mice skin, it indicates that the EGFP protein is introduced into the epidermis, but not into the deeper tissues (e.g. muscle tissue).

Gene Transformation with Naked DNA Solution or DNA Coated Particles 4 week-old Balb/c mice are selected and the abdominal skin of the mice is bombarded by the gene gun with a helium pressure of 60 psi, using either the naked DNA sample solution without metal particle carriers (DNA solution group) or DNA-coated gold particles sample (particle group). The particle-free DNA solution contains 0.2 μg pEGFP-N2 vector, while the DNA-coated particle sample includes 0.2 μg pEGFP-N2 vector/0.1 mg gold particles coated by spermidine/$CaCl_2$. The next day after the bombardment, the abdominal skin of the mice from two groups is removed and observed the fluorescence under fluorescence microscopy.

Figure 7:
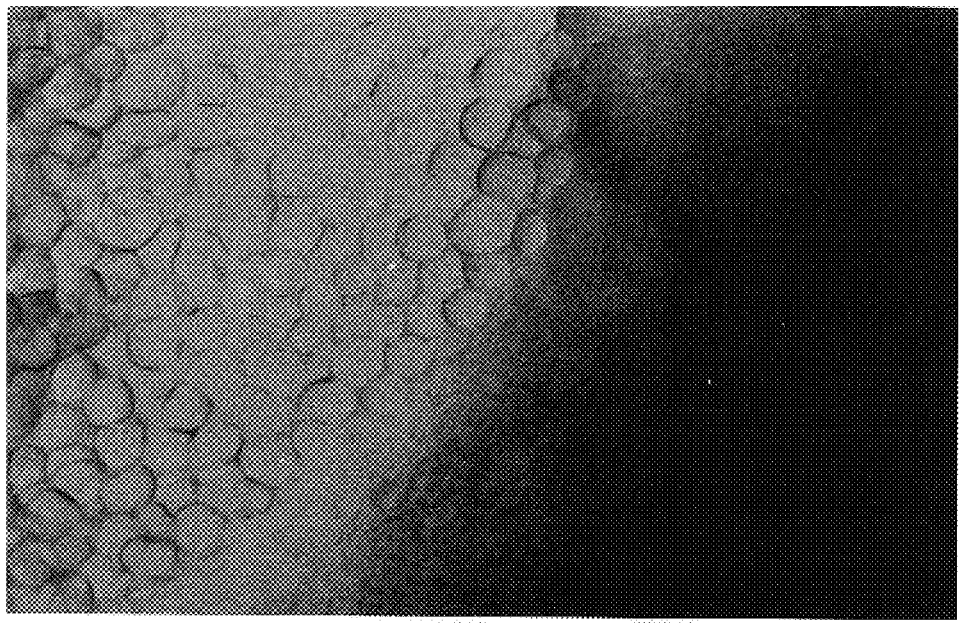
FIG. 7 is a magnified view (40×) of abdominal epidermis cells of a mouse subsequent to DNA solution bombardment using the gene gun of the present invention.

FIG. 7 is a magnified view (40×) of abdominal epidermis cells of a mouse subsequent to DNA solution bombardment using the gene gun of the present invention. The fluorescence present in the cells represents successful transformation by the pEGFP-N2 vector for the cells. The observed fluorescence is prominent and uniform.

Figure 8:
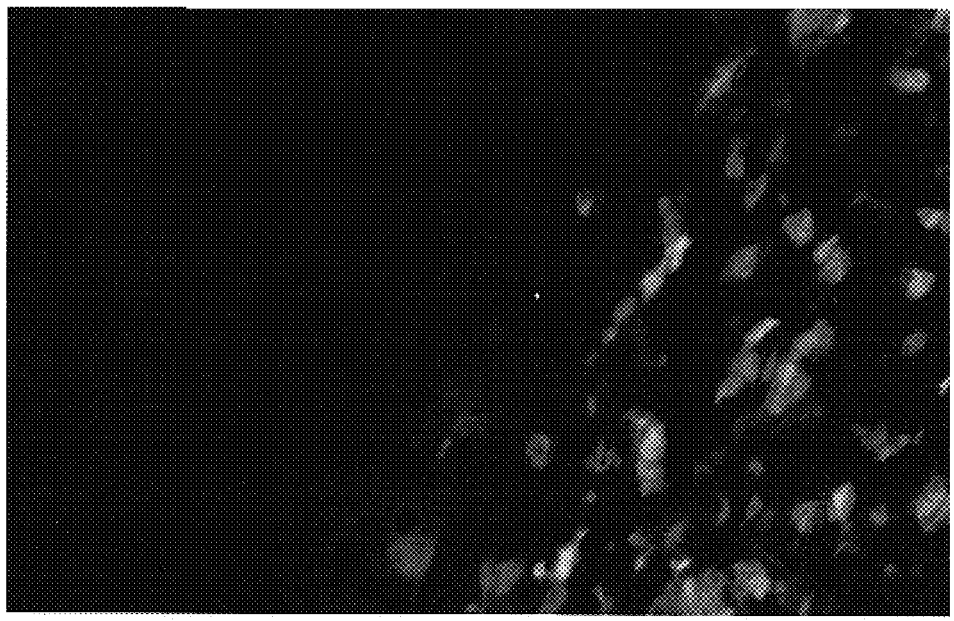
FIG. 8 is a magnified view (40×) of abdominal epidermis cells of a mouse subsequent to bombardment with DNA-coated particles using the gene gun of the present invention.

FIG. 8 is a magnified view (40×) of abdominal epidermis cells of a mouse subsequent to bombardment with DNA-coated particles. On the other hand, the observed fluorescence is weak and distributes sparsely.

Compare the results of the above two groups, it shows that a better transformation efficacy is achieved by the bombardment of the gene gun using the naked DNA solution.

Western Blotting of Mice Genetic Immunization by Naked DNA 4 week-old Balb/c mice are selected and shaved to expose the abdominal skin. After filling naked DNA sample solution (solution group) or DNA-coated gold particles (particle group) into the gene gun, bombardment is performed to the mice skin and the resultant immune responses from two groups are compared.

The abdominal skin of the mice is bombarded by the gene gun once per week for 4-6 weeks and the bombardment is performed with a helium pressure of 80 psi. For the solution group, the bombardment is performed with naked DNA solution once per week for 4 weeks, one shot containing 1.8 μg naked pEGFP-N2 vector. For the particle group, the bombardment is performed with DNA coated gold particles once per week for 6 weeks, one shot containing 0.6 μg naked pEGFP-N2 vector/0.6 mg gold particles. From the 1st to 5th week, blood serum is collected once per week. Serum is then analyzed by Western Blotting to see whether the anti-EGFP antibody exists.

Figure 9:
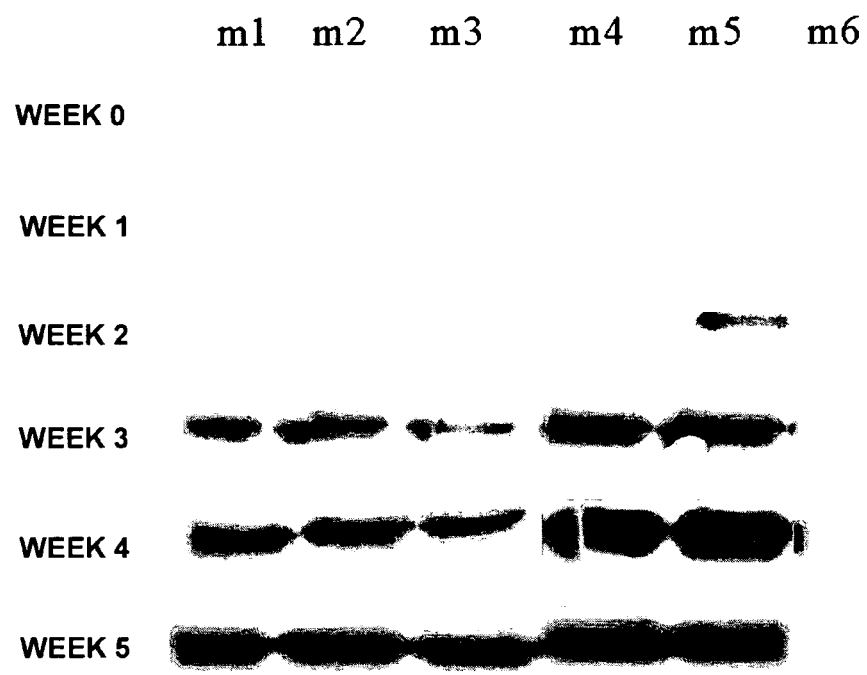
FIG. 9 shows the western blotting result for monitoring the immune response of the mouse subsequent to DNA solution bombardment using the gene gun of the present invention.

Results of the solution group are shown in FIG. 9. Mice m1-m5 were immunized with naked DNA solution (pEGFP-N2), while mouse m6 is the control, immunized with water, as having no immunization. Mice m1-m5 were observed with medium antibody reaction after the second boost (the $3^{rd}$ week), while mouse m5 was observed with weak antibody reaction in the $2^{nd}$ week.

Figure 10:
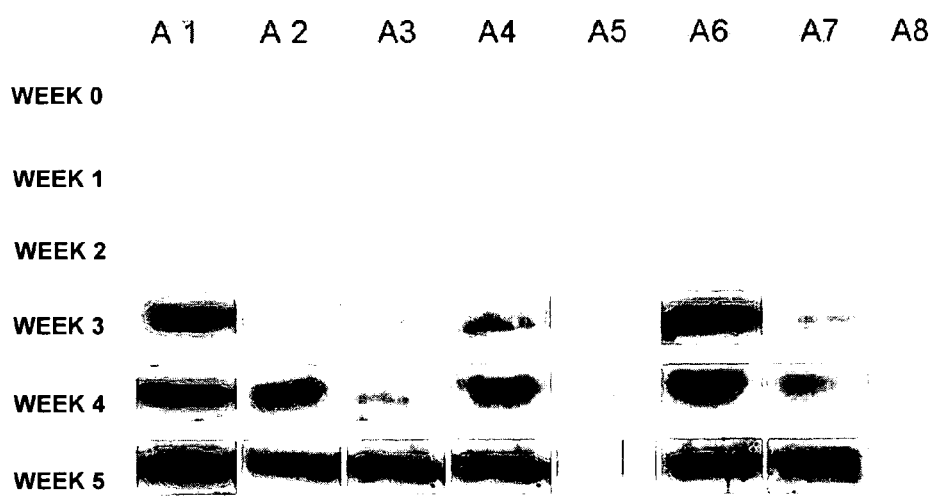
FIG. 10 shows the western blotting result for monitoring the immune response of the mouse subsequent to bombardment with DNA-coated particles using the gene gun of the present invention.

Results of the particle group are shown in FIG. 10. Mice A5 and A8 are the control, immunized with water, as having no immunization. For mice A1-A4 and A6-A7, medium antibody reaction is generally observed in the $4^{th}$ or $5^{th}$ week, although mouse A7 is observed with small antibody reaction in the $2^{nd}$ week.

In general, the immunization induced by the naked DNA solution seems to be slightly superior, when the immunization results of the gene gun with naked DNA solution and with DNA-coated particles. Both can induce antibody reaction in $3^{rd}$ to $4^{th}$ week after the bombardment.

Accordingly, the contour design of the spray nozzle of the gene gun and modification of the gene gun operation allows the gene gun to operate at a lower pressure and accelerate the sample solution to an extreme high speed. Without being carried by the metal particles, the biological materials can penetrate the epidermis or the cell/membrane/wall and enter into the cell or the organism.

Since a low pressure is used, the biological materials are driven into the cell without using metal particles, to achieve gene transformation with minimal noise and damages to the cells. Moreover, since the sample of this invention is prepared in the solution form without using metal particles, the operation of the gene gun is easy and straightforward, disregarding the difficulties conventionally encountered in the preparation of the gold particles. In the present invention, the biological material, for example, DNAs, RNAs, proteins, virions or drugs, is prepared in the solution form and accelerated to enter into the cell for delivery or gene transformation.

Moreover, due to the contour design of the spray nozzle, the operation of the gene gun is modified to allow an even distribution of the sample solution. Since the pressure at the nozzle opening is close to atmospheric pressure, the target cell is prevented from being damaged.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for delivering a biological material using a gene gun, comprising:
   providing the gene gun comprising a pressurized chamber, a sprayer, a controller valve and a material delivery system;
   placing a sample solution into the material delivery system, wherein the sample solution comprises at least the biological material;
   triggering the gene gun and providing a gas through the controller valve to the pressurized chamber until the gas establishes a pressure equal to or lower than 100 psi;
   releasing the sample solution from the material delivery system, so that the sample solution is accelerated by the gas in the pressurized chamber; and
   discharging the sample solution out of the sprayer, wherein the sprayer includes a spray nozzle and a spray tube, and the spray nozzle comprises an interior contour, wherein the interior contour of the spray nozzle comprises a diverging part, a converging part and a spray neck positioned between the diverging part and the converging part and connected to the material delivery system, wherein the sample solution is released from the material delivery system around the spray neck of the spray nozzle and is released in a direction perpendicular to a direction of the flow of the gas, and the spray tube is a diverging straight tube, so that the biological material is evenly injected into a target,
   wherein the biological material is delivered without using micro-carriers or particle carriers.

2. The method of claim 1, wherein the biological material is a nucleic acid.

3. The method of claim 1, wherein the biological material is a protein.

4. The method of claim 1, wherein the biological material is a virion.

5. The method of claim 1, wherein the biological material is a vaccine.

6. The method of claim 1, wherein the biological material is an immunogen.

7. The method of claim 1, wherein the sample solution is accelerated to a speed of 200-300 m/s by the gas.

8. The method of claim 1, wherein a pressure at the sprayer's outlet is about 1 atmospheric pressure.

9. The method of claim 1, wherein a range of the interior contour of the converging part includes:
   rt<Rt<2rt, wherein Rt represents a curvature radius of the converging part, rt is a radius of the spray neck; and
   wherein θ<15 degrees, wherein θ is an angle between the diverging part and a center axis of the spray tube.

10. The method of claim 1, wherein the gas includes a nitrogen gas or a helium gas.

11. A method for gene transformation by using a gene gun, comprising:
    providing the gene gun comprising a pressurized chamber, a sprayer, a controller valve and a material delivery system;
    placing a sample solution into the material delivery system, wherein the sample solution comprises at least a nucleic acid;
    triggering the gene gun and providing a gas through the controller valve to the pressurized chamber to establish a pressure equal to or lower than 100 psi, wherein the gas is a nitrogen gas or a helium gas;
    releasing the sample solution from the material delivery system after the gas in the pressurized chamber establishes the pressure, so that the sample solution is accelerated by the gas in the pressurized chamber; and
    discharging the sample solution out of the sprayer, wherein the sprayer includes a spray nozzle and a spray tube, and the spray nozzle comprises an interior contour, wherein the interior contour of the spray nozzle comprises a diverging part, a converging part and a spray neck positioned between the diverging part and the converging part and connected to the material delivery system, wherein the sample solution is released from the material delivery system around the spray neck of the spray nozzle and is released in a direction perpendicular to a direction of the flow of the gas, and the spray tube is a diverging straight tube, so that the nucleic acid is evenly injected into a target,
wherein the nucleic acid is delivered without using microcarriers or particle carriers.

12. The method of claim 11, wherein the sample solution is accelerated to a speed of 200-300 m/s by the gas.

13. The method of claim 11, wherein a pressure at the sprayer's outlet is about 1 atmospheric pressure.

14. The method of claim 11, wherein a range of the interior contour of the converging part includes:
rt<Rt<2rt, wherein Rt represents a curvature radius of the converging part, rt is a radius of the spray neck; and
wherein θ<15 degrees, wherein θ is an angle between the diverging part and a center axis of the spray tube.

* * * * *

UNITED STATES PATENT AND TRADEMARK OFFICE
CERTIFICATE OF CORRECTION

PATENT NO. : 7,638,332 B2  Page 1 of 1
APPLICATION NO. : 10/735602
DATED : December 29, 2009
INVENTOR(S) : Lin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 371 days.

Signed and Sealed this

Ninth Day of November, 2010

David J. Kappos
*Director of the United States Patent and Trademark Office*